United States Patent [19]
Giovanella et al.

[11] Patent Number: 5,889,017
[45] Date of Patent: *Mar. 30, 1999

[54] METHOD FOR TREATING CANCER WITH WATER-INSOLUBLE S-CAMPTOTHECIN OF THE CLOSED LACTONE RING FORM AND DERIVATIVES THEREOF

[75] Inventors: Beppino C. Giovanella, Houston; Hellmuth R. Hinz, Kingwood; Anthony J. Kozielski, Springs, all of Tex.

[73] Assignee: The Stehlin Foundation for Cancer Research, Houston, Tex.

[ * ] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. Nos. 5,552,154 and 5,652,244.

[21] Appl. No.: 767,861

[22] Filed: Dec. 17, 1996

Related U.S. Application Data

[63] Continuation of Ser. No. 474,761, Jun. 7, 1995, which is a continuation of Ser. No. 301,727, Sep. 7, 1994, Pat. No. 5,552,154, which is a continuation of Ser. No. 2,844, Jan. 15, 1993, abandoned, which is a continuation-in-part of Ser. No. 820,334, Jan. 14, 1992, abandoned, which is a continuation-in-part of Ser. No. 432,066, Nov. 6, 1989, Pat. No. 5,225,404.

[51] Int. Cl.⁶ ................................................... A61K 31/44
[52] U.S. Cl. ................................................................ 514/283
[58] Field of Search ................................................ 514/283

[56] References Cited

U.S. PATENT DOCUMENTS

| | | | |
|---|---|---|---|
| Re. 32,518 | 10/1987 | Miyasaka et al. | 546/48 |
| 3,894,029 | 7/1975 | Winterfeldt et al. | 424/258 |
| 4,031,098 | 6/1977 | Sugasawa | 424/258 |
| 4,357,422 | 11/1982 | Giard et al. | 435/68 |
| 4,399,276 | 8/1983 | Miyasaka et al. | 546/48 |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 |
| 4,604,463 | 8/1986 | Miyasaka et al. | 546/48 |
| 4,774,236 | 9/1988 | Cook et al. | 546/48 |
| 4,867,978 | 9/1989 | Gold | 424/166 |
| 4,874,779 | 10/1989 | Senter | 514/410 |
| 4,894,456 | 1/1990 | Wall et al. | 546/48 |
| 4,904,768 | 2/1990 | Saulnier et al. | 536/17.1 |
| 4,914,205 | 4/1990 | Sawada et al. | 546/48 |
| 4,939,255 | 7/1990 | Tagawa et al. | 546/48 |
| 4,943,579 | 7/1990 | Vishnuajjala et al. | 514/283 |
| 4,981,968 | 1/1991 | Wall et al. | 546/48 |
| 5,004,758 | 4/1991 | Boehm et al. | 514/283 |
| 5,041,424 | 8/1991 | Saulnier et al. | 514/27 |
| 5,049,668 | 9/1991 | Wall et al. | 546/48 |
| 5,053,512 | 10/1991 | Wani et al. | 546/48 |
| 5,061,795 | 10/1991 | Tagawa et al. | 546/48 |
| 5,061,800 | 10/1991 | Yaegashi et al. | 546/48 |
| 5,064,823 | 11/1991 | Lee et al. | 514/198 |
| 5,106,742 | 4/1992 | Wall et al. | 514/283 |
| 5,122,526 | 6/1992 | Wall et al. | 546/48 |
| 5,122,606 | 6/1992 | Wani et al. | 546/48 |
| 5,126,351 | 6/1992 | Luzzio et al. | 514/241 |
| 5,145,684 | 9/1992 | Liversidge et al. | 424/489 |
| 5,155,225 | 10/1992 | Fortunak et al. | 546/48 |
| 5,162,532 | 11/1992 | Comins et al. | 546/48 |
| 5,180,722 | 1/1993 | Wall et al. | 514/219 |
| 5,225,404 | 7/1993 | Giovanella et al. | 514/283 |

FOREIGN PATENT DOCUMENTS

| | | |
|---|---|---|
| 0 074 256 | 3/1983 | European Pat. Off. . |
| 0 220 601 | 5/1987 | European Pat. Off. . |
| 0 418 099 A2 | 3/1991 | European Pat. Off. . |
| 0 540 099 A1 | 5/1993 | European Pat. Off. . |
| 61-50985 | 3/1983 | Japan . |
| 59-5188 | 1/1984 | Japan . |
| 59-501288 | 3/1984 | Japan . |
| 59-51289 | 3/1984 | Japan . |
| 61-85319 | 4/1986 | Japan . |
| 61-85389 | 4/1986 | Japan . |
| WO 91 05556 | 5/1991 | WIPO . |
| WO 91/16904 | 11/1991 | WIPO . |

OTHER PUBLICATIONS

Cancer Research 5. 3980–3987, Jul. 15, 1992; "Complete Inhibition of Growth followed by Death of Human Malignant Melanoma Cells in Vitro and Regression of Human Melanoma Xenografts in Immunodeficient Mice Induced by Camptothecins[1]".

1992 AACR Abstract Form, "Pharmacokinetics of Tritum Labeled Camptothecin in Nude Mice," Smith, P.L. et al.

1992 AACR Abstract Form, "Growth Inhibition of Human Cancer Metasteses in the Xenograft Model by Camptothecin [NSC 94600], 9–amino–(NSC 60371) and 9–nitrocamptothecin," Potmesil, M.

Giovanella et al., Cancer Research, vol. 51, pp. 3052–3055, Jun. 1, 1991.

Kharbanda et al., Cancer Research, vol. 51, pp. 6636–6642, Dec. 15, 1991.

*The Alkaloids,* vol. XXV, Chapter 1, "Antitumor Alkaoids," Suffness et al., pp. 73–89, copyright 1985, Academic Press, Inc.

Wall et al., "New Type of 9–Nitrocamptothecin and a Method of its Production," J. Am. Chem. Soc., vol. 88, No. 16, pp. 3888–3890, Aug. 20, 1966.

Hsiang, Y.–H. et al., Cancer Res. 48: 1722–1726, 1988.
Wani, M.C. et al., J. Med. Chem. 30: 1774–1779, 1987.
Wani, M.C. et al., J. Med. Chem 29:2358–2363, 1986.
Hsiang, Y.–H. et al., J. Biol. Chem 97: 14873–14878, 1985.
Hsiang, Y.–H. et al., Abstract 683 from The American Association for Cancer Research, vol. 29, Mar. 1988.

(List continued on next page.)

*Primary Examiner*—Jerome D. Goldberg
*Attorney, Agent, or Firm*—Armstrong, Westerman, Hattori, McLeland & Naughton

[57] ABSTRACT

A method of treating specific forms of cancer with water-insoluble 20(S)-camptothecin compounds with the closed-lactone ring intact and/or derivatives thereof is disclosed. The method includes administering the compounds intramuscularly, orally and transdermally.

27 Claims, 10 Drawing Sheets

OTHER PUBLICATIONS

Wall, M.E. et al., J. Med. Chem. 29: 1553–1555, 1986.
Nelson, W.G. et al., Cancer Res. 47:3246–3250, 1987.
Hsiang Y.-H. et al., Cancer Res. 49: 4386–4389, 1989.
Wani, M.C. et al., J. Med. Chem. 30: 2317–2319, 1987.
Giovanella, B.C. et al., Cancer 52: 1146–1152, 1983.
Wani, M.C. et al., J. Med. Chem. 30: 1774–1779, 1987.
Wani, M.C. et al., J. Med. Chem. 23: 554–560, 1980.
Leibovitz, A. et al., Cancer Res. 36: 4562–4569, 1976.
Fogh, J. et al., in "Human Tumor Cells In Vitro," Fogh, Jr. et al., Plenum Press, New York, 1976, pp. 115–141.
Liu, L.F. et al., Proc. Nat'l. Acad. Sci. USA, 78: 3487–3491, 1981.
Muggla, F.M. et al., Cancer Chemo. Rep. 56: 515–521, 1972.
Gottlieb, J.A. et al., Cancer Chemo. Rep. 54: 461–470, 1970.
Jaxel,C. et al., Cancer Res. 49: 1465–1469, 1989.
Potmesil, M. et al., Cancer Res. 48:3537–3543, 1988.
Chemical Abstracts, vol. 106(25), Abstract No. 207285z (1987).
Chemical Abstracts, vol. 106(15), Abstract No. 120133z (1987).
Chemical Abstracts,vol. 106(15), Abstract No. 11479a (1987).
Chemical Abstracts,vol. 106(13), Abstract No. 95753s (1987).
Chemical Abstracts, vol. 103(9), Abstract No. 64374c (1985).
Chemical Abstracts, vol. 101, Abstract No. 130677r (1984).
Chemical Abstracts, vol. 101(11), Abstract No. 91322z (1982).
Chemical Abstracts, vol. 101(10), Abstract No. 78770z (1984).
Chemical Abstracts, vol. 100(21), Abstract No. 167724j (1983).
Chemical Abstracts, vol. 100, Abstract No. 139434w (1984).
Chemical Abstracts, vol. 97, Abstract No. 188278b (1982).
Chemical Abstracts, vol. 96(9), Abstract No. 69271p (1981).
Chemical Abstracts, vol. 95(15), Abstract No. 133209h (1981).
Chemical Abstracts, vol. 94(1), Abstract No. 4143n (1980).
Chemical Abstracts, vol. 92(5), Abstract No. 37766e (1980).
Chemical Abstracts, vol. 92(3), Abstract No. 18799b (1980).
Chemical Abstracts, vol. 90(4), Abstract No. 28930k (1979).
Chemical Abstracts, vol. 90(3), Abstract No. 22857v (1979).
Chemical Abstracts, vol. 84, Abstract No. 115629p (1976).
Chemical Abstracts, vol. 94(12), Abstract No. 90169e (1980).
Derwent 89–179979/25.
Nicholas et al., J. Med. Chem., vol. 33, No. 3, pp. 972–978, 1990.
Ohro et al., Proc. Ann. Meet. Am. Soc. Clin. Oncol., 8: A1019, 1989.
Hertzberg et al., J. Med. Chem., vol. 32(3), pp. 715–720, 1989.
Hsiang et al., Proc. Ann. Meet. Am. Assoc. Cancer Res., 30: A2476, 1989.
Hertzberg et al., Proc. Ann. Meet. Am. Assoc. Cancer Res., 30: A2485, 1989.
Pommier et al., Proc. Ann. Meet. Am. Assoc. Cancer Res., 29: A1080, 1988.
Lin et al., Yao Hsueh Hsueh Pao; vol. 23(3), pp. 186–188 (1988).
Ronman et al., Journal of Labelled Compounds and Radiopharmaceuticals, vol. 18(3), pp. 319–329, 1981.
Danishefky et al., J. Org. Chem., vol. 39(28), pp. 3430–3432, 1974.
Plattner et al., J. Org. Chem., vol. 39(3), pp. 303–311, 1974.
Plattner et al., J. Amer. Chem. Soc., vol. 94(24), pp. 8615–8616, 1972.
Govindachari et al., "9–Methoxycamptothecin: a New Alkaloid from Mappie voetida Miers," pp. 453–454.
Giovanella et al., Science, vol. 246, pp.1046–1048, 1989.
Xi–Ran et al., "Topical Camptothecine in Treatment of Psoriasis," Int'l. Journal of Dermatology, vol. 27, No. 7, pp. 475–476, Sep. 1988.
Ching–jung et al., "Effect of Topical Use of Camptothecine–Dimethyl Sulfoxide Solution in Psoriasis," Chinese Medical Journal, vol. 1, No. 5, pp. 355–360, Sep. 1975.
Tung et al., "Camptothecin Instillation and Local Injection for Prevention and Treatment of Urinary Bladder Tumors," Chinese Medical Journal, vol. 92, No. 1, pp. 57–60, 1979.
Pantazis et al., "Complete Inhibition of Growth Followed by Death of Human Malignant Melanoma Cells in Vitro and Regression of Human Melanoma Xenografts in Immunodeficient Mice Induced by Camptothecin," Cancer Research, vol. 52, No. 14, pp. 3980–3987 Jul. 15, 1992.

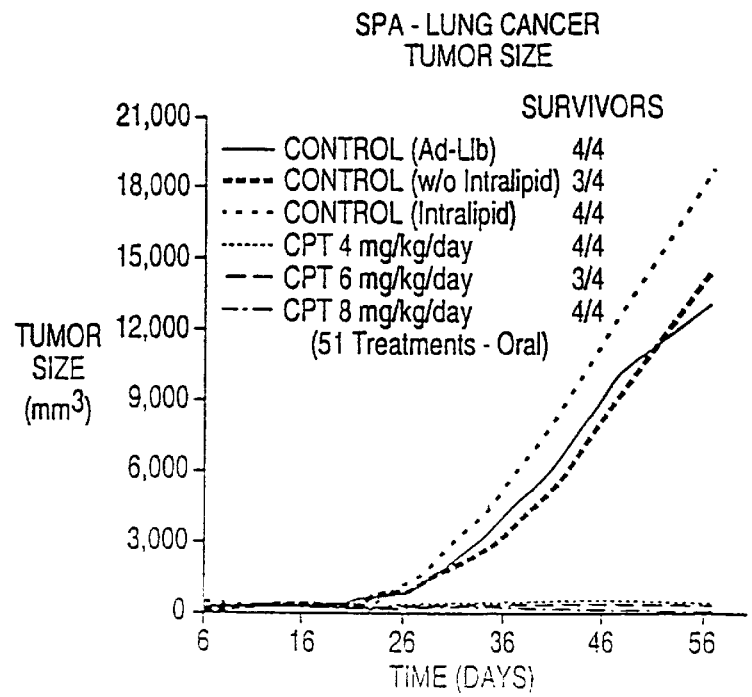
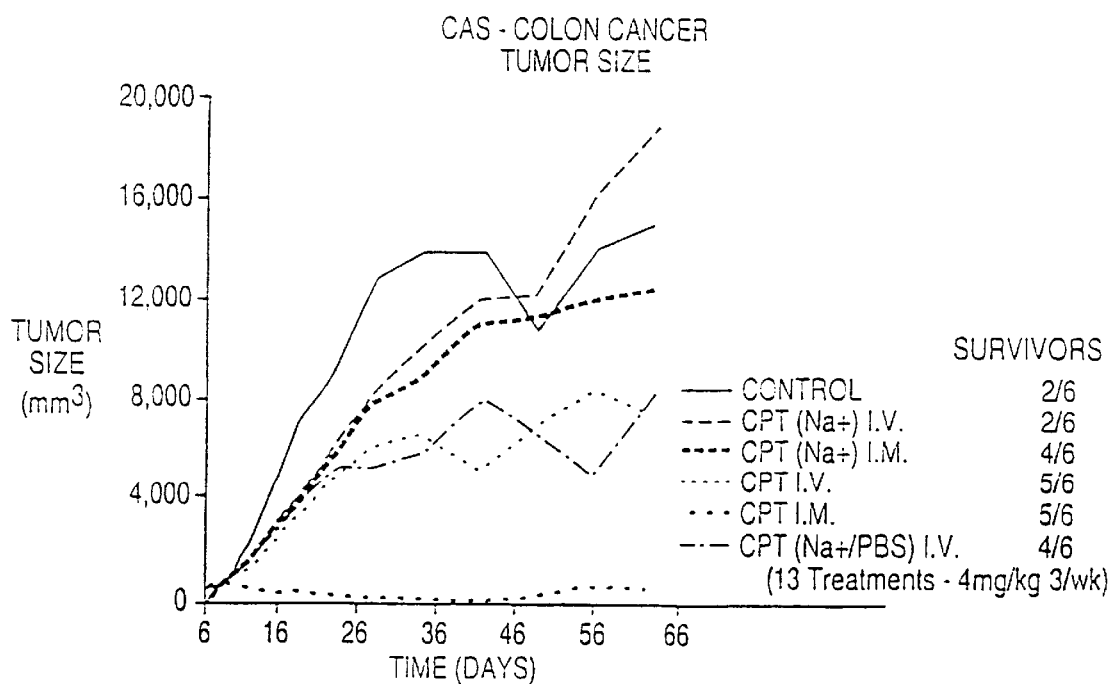

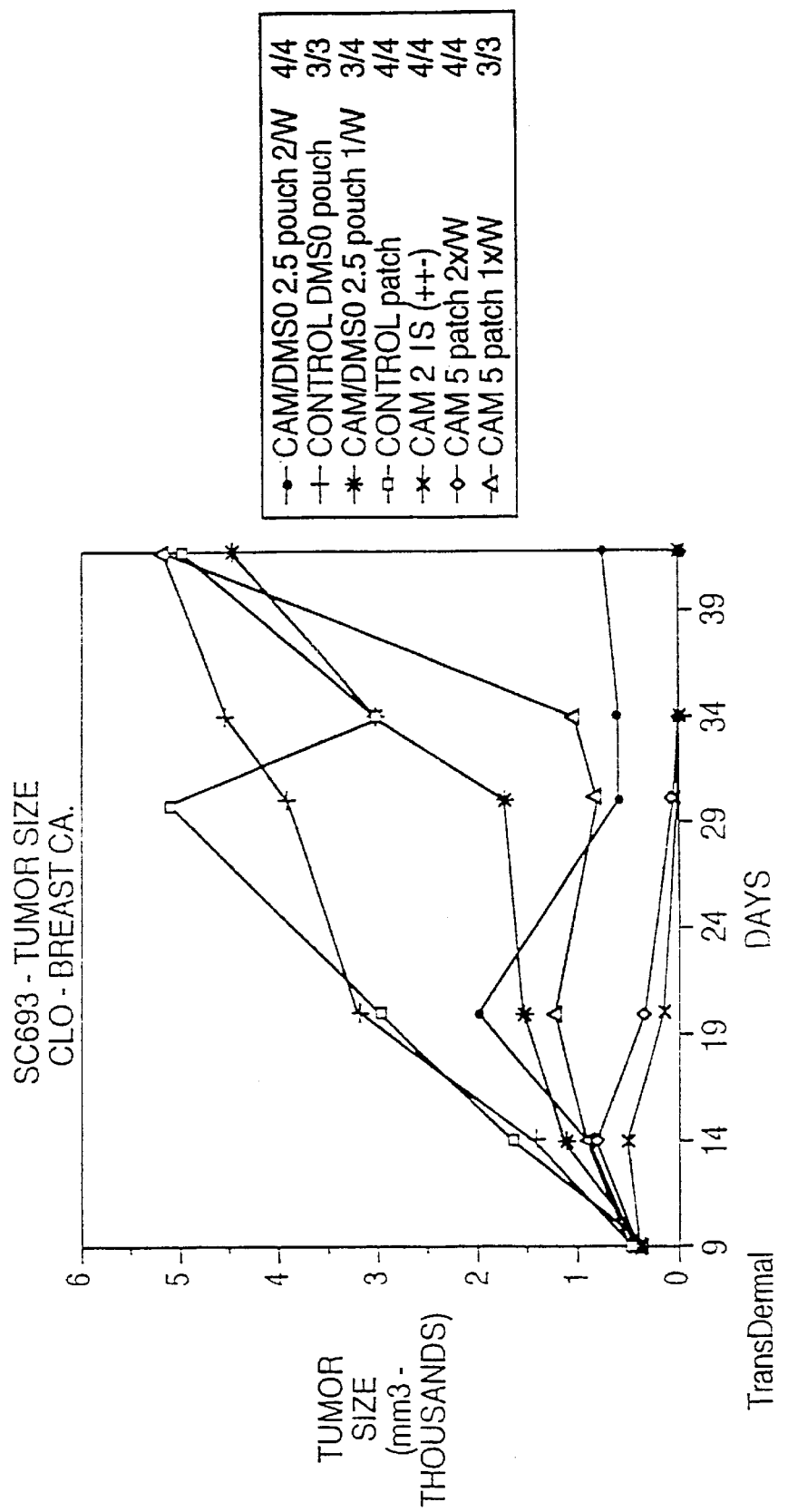

METHOD FOR TREATING CANCER WITH WATER-INSOLUBLE S-CAMPTOTHECIN OF THE CLOSED LACTONE RING FORM AND DERIVATIVES THEREOF

This is a continuation of application Ser. No. 08/474,761, filed Jun. 7, 1995, which was a continuation of application Ser. No. 08/301,727, filed Sep. 7, 1994, now U.S. Pat. No. 5,552,154; which was a continuation of application Ser. No. 08/002,844, filed Jan. 15, 1993, abandoned; which was a continuation-in-part of application Ser. No. 07/820,334, filed Jan. 14, 1992, abandoned; which was a continuation-in-part of application Ser. No. 07/432,066, filed Nov. 6, 1989, now U.S. Pat. No. 5,225,404.

FIELD OF THE INVENTION

The present invention relates to a method for treating cancer in mammals, more particularly, to a method for treating malignant tumors such as lung, breast, stomach, pancreatic, prostate, bladder, osteosarcoma and ovary carcinomas and malignant melanomas.

BACKGROUND OF THE INVENTION

20(S)-camptothecin (CPT), a plant alkaloid, was found to have anticancer activity in 1966 (Wall, M., Wani, M. C., Cooke, C. E., Palmer, K. H., McPhail, A. T. and Slim, G. A. "Plant antitumor agents. I. The isolation and structure of camptothecin, a novel alkaloidal leukemia and tumor inhibitor from *Camptotheca acuminata*", *J. Am. Chem. Soc.* 88: 3888–3890, 1966).

During the sixties and seventies the sodium salt of CPT was derived from CPT, and clinical trials of this chemically altered CPT were carried out and then abandoned because of the high toxicity and low potency of this compound (Gottlieb, J. A., Guarino, A. M., Call, J. B., Oliverio, V. T. and Block, J. B. "Preliminary pharmacological and clinical evaluation of camptothecin sodium salt (NSC 100880)", *Cancer Chemother. Rep.* 54: 461–470; 1979; Muggia, F. M., Creaven, P. J., Hansen, H. H., Cohen, M. N. and Selawry, D. S. "Phase I clinical trials of weekly and daily treatment with camptothecin (NSC 100880). Correlation with clinical studies." *Cancer Chemother. Rep.* 56: 515–521; 1972; Gottlieb, J. A. and Luce, J. K. "Treatment of malignant melanoma with camptothecin (NSC 100880)." *Cancer Chemother. Rep.* 56: 103–105; 1972; and Moertel, C. G., Schutt, A. J., Reitemeier, R. J. and Hahn, R. G. "Phase II study of camptothecin (NSC 100880) in the treatment of advanced gastrointestinal cancer." *Cancer Chemother. Rep.* 56: 95–101; 1972. All these trials were conducted using the hydrosoluble, sodium salt derivative of CPT (CPT Na+), which was administered via i.v. The research of the present inventors has fully confirmed the ineffectiveness and the toxicity of CPT Na+.

Experiments have demonstrated that the non-water soluble CPT is nontoxic and highly effective as an anticancer agent. Furthermore, the present inventors have demonstrated that the intramuscular and oral administration provide unexpectedly better results than the intravenous administration.

Drug therapies have been evaluated with respect to treating human cancer, e.g., human cancer xenograft lines. Human tumors are serially heterotransplanted into immunodeficient, so-called "nude" mice, and the mice then tested for their responsiveness to a specific drug. (Giovanella, B. C., et al., *Cancer* 52(7):1146 (1983)). The data obtained in these studies strongly support the validity of heterotransplanted human tumors into immunodeficient mammals, such as nude mice, as a predictive model for testing the effectiveness of anticancer agents.

It was determined that 9-Amino-20(S)-Camptothecin (9AC) and 10,11-Methylendioxy-20(S)-Camptothecin (10, 11MD) are capable of having high anticancer activity against human colon cancer xenografts (Giovanella, B. C., Wall, M. E., Wani, M. C., Nicholas, A. W., Liu, L. F., Silber, R. and Potmesil, M. "Highly effective topoisomerase-I targeted chemotherapy of human colon cancer in xenografts." *Science* 246: 1046–1048; 1989). After this finding, the present inventors extended these studies to other human cancers growing as xenografts in nude mice as well as conducted studies on the administration of CPT and its derivatives. It is important to note that the fundamental difference between the chemical used by the present invention (CPT) and the one used ineffectively and with high attendant toxicity in the past (CPT Na+) is that CPT is water-insoluble and CPT Na+is water-soluble.

SUMMARY OF THE INVENTION

An object of the present invention is to provide a novel method for treating cancers in mammals.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a method for treating malignant tumors in a mammal which comprises administering intramuscularly, orally or transdermally an effective amount of a water-insoluble 20(S)-Camptothecin (CPT) with the closed-lactone ring intact or a derivative thereof or a mixture thereof.

It is to be understood that both the foregoing general description and the following detailed description are exemplary and explanatory only and are not restrictive of the present invention, as claimed.

BRIEF DESCRIPTION OF THE DRAWINGS

FIG. 2 shows the results obtained for SPA lung adenocarcinomas in nude mice treated daily with CPT in Intralipid 20 administered orally at various doses.

FIG. 3 shows the results obtained for CAS colon carcinoma in nude mice treated twice a week with CPT or its sodium salt (CPT Na+) both at the dose of 4 mg/kg intravenously or intramuscularly. All treatments in Intralipid 20 except for a group treated with CPA Na+in Phosphate Buffered Saline (PBS).

FIGS. 16 and 17 are graphs which show the results obtained for CLO breast carcinoma in nude mice treated with 20(S)-CPT or CPT derivatives by transdermal application.

DESCRIPTION OF THE PREFERRED EMBODIMENT(S)

Figure 1A:
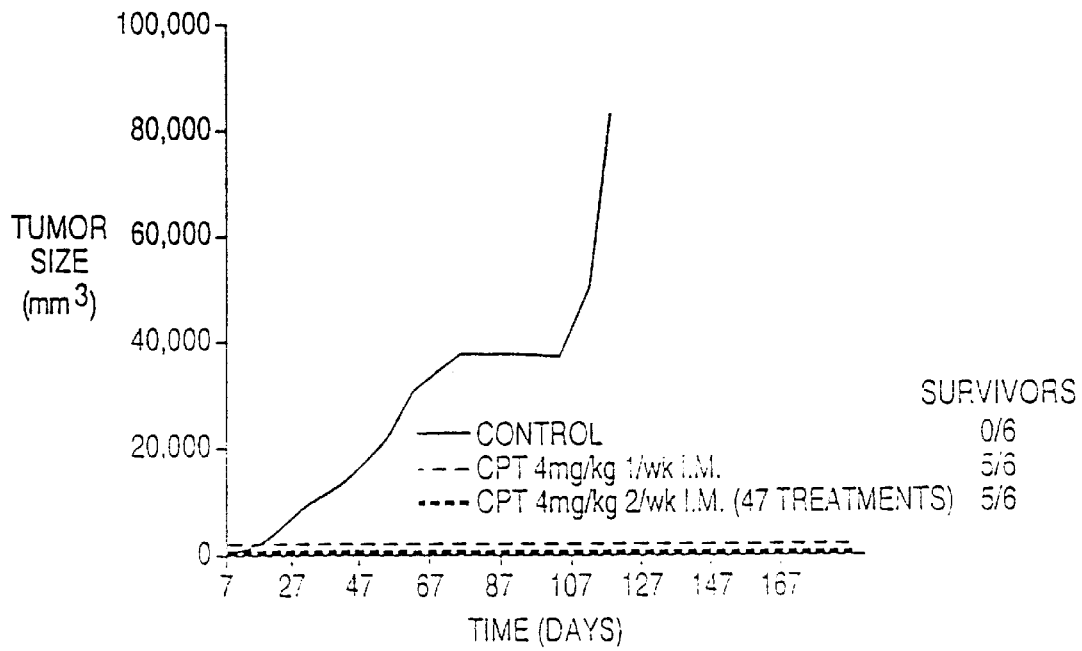
FIG. 1a shows the results obtained for CLO breast carcinomas in nude mice treated once a week and twice a week with a suspension of 20(S)-Camptothecin (CPT) in Intralipid 20 intramuscularly at the dose of 4 mg/kg. The tumor size was measured in $mm^3$ in function of time.

CPT is a plant alkaloid isolated from *Camptotheca acuminata*. Chemical derivatives of CPT can be prepared either in a semisynthetic or totally synthetic way. (See, e.g., Wani, M. C. et al., *J. Med. Chem.* 23:544, 1980; Wani, M. C. et al., *J. Med. Chem.* 30: 1774 (1987); and Wani, M. C. et al., *J. Med. Chem.* 30: 2317 (1987)).

In the examples discussed below, the CPT was obtained from the Institute of Materia Medica, Academia Sinica, Shanghai, China, and further purified using standard chromatographic techniques. Camptothecin Sodium Salt (CPT Na+), 9-Nitro-20(S)-Camptothecin ($9NO_2$) and 9-Amino-20 (S)-Camptothecin (9AC) were also synthesized from CPT. CPT and derivatives thereof have to be extensively purified prior to administering for use in the present invention because: (1) the natural product contains several other components which have a large degree of toxicity for example, in mice, and (2) FDA regulations require such purifying for any drug or compound to be used as a medicine. Methods of purification known by those skilled in the art can be used, e.g.—dissolving the CPT in a suitable solvent such as chloroform or methylene chloride and then adsorbing onto a column containing silica gel and then carrying out elution of the adsorbed materials by increasing the polarity of the eluant by adding, e.g., methanol.

The purity of the compound can be tested by high performance liquid chromatography (HPLC) and thin layer chromatography (TLC) and other appropriate methods known in the art. The compound can also be completely characterized using infrared (IR), ultraviolet (UV) and nuclear magnetic resonance (NMR) spectroscopy and elemental analysis.

Furthermore, the CPT and derivatives thereof used in the present invention are water-insoluble and not administered in the chemically and physically different sodium salt form. This difference can easily be observed by looking at their elemental analysis, NMR, UV and IR spectra and also by their different physical behavior in HPLC and TLC experiments.

CPT and derivatives thereof of the closed lactone ring form are used and are administered intramuscularly or orally, and in such cases it was possible to obtain total remissions of a vast spectrum of human cancers without the toxicity observed previously with CPT Na+. The derivatives of CPT for use in the present invention include, for example, $9NO_2$, and 9AC. A mixture of CPT and derivatives thereof can also be used in the present invention.

Other related derivatives can also be used in conjunction with the method of the present invention. Examples include dimethylaminomethyl-10-hydroxy-20(S)-CPT (topotecan), 7-ethyl-10-[4-(1-piperdino)-1-piperdino]-carbonyloxy-CPT (CPT-11), 7-ethyl-10-hydroxy-20(S)-CPT, 9-amino-20(S)-CPT, 9-nitro-20(S)-CPT, 10,11-methylenedioxy-20(S)-CPT, 9-chloro-20(S)-CPT, 9-bromo-20(S)-CPT, 9-hydroxy-20(S)-CPT, 11-hydroxy-20(S)-CPT, and 10-hydroxy-20(S)-CPT.

Another method of administering the compounds of the present invention is by a transdermal or transcutaneous route. One example of such an embodiment is the use of a patch. In particular, a patch can be prepared with a fine suspension of a compound disclosed in the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the CPT compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

In the studies, the water-soluble derivatives of these compounds proved to be ineffective as anticancer agents and very toxic to mammals. Even the closed lactone ring forms of CPT and derivatives thereof showed a great difference in activity, depending on their route of administration. In the studies, the intramuscular, transdermal and oral routes were unexpectedly superior to other routes of delivery.

As used herein, the term "malignant tumor" is intended to encompass all forms of human carcinomas, sarcomas and melanomas which occur in the poorly differentiated, moderately differentiated, and well differentiated forms.

In treating or retarding malignant tumors in mammals in accordance with the present invention, the aforedescribed camptothecin compounds are administered intramuscularly, transdermally or orally, using commonly known methods, for example, gelatin capsules for oral administration, as well as novel, superior formulations, such as microsuspensions in lipid and in lipid-like emulsions (e.g.—Intralipid 20, cottonseed oil and peanut oil) for intramuscular administration and inclusion in cholesterol pellets for subcutaneous long-term administration.

As used herein, an "effective amount" of CPT and derivatives thereof described above is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages for animals of various sizes, species and humans (based on $mg/M^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537–538 (1970). An effective amount of the camptothecin compounds in the present invention can range from about 12.5 mg/m$^2$ of body surface per day to about 31.3 mg/m$^2$ of body surface per day.

The preferred effective amounts or dosages of CPT and/or derivatives thereof in mice are about 1 to about 4 mg CPT/kg of body weight twice a week for an intramuscular route and about 0.75 to about 1.5 mg CPT/kg/day for the oral route. Effective amounts or dosages of CPT and/or derivatives thereof in mice are, for instance about 1.5 mg/Kg/week to about 10 mg/Kg/week CPT for the transdermal route. For all of the administering routes, the exact timing of administration of the dosages can be varied to achieve optimal results. Generally, when using Intralipid 20 as the carrier for the CPT, the actual dosage of CPT reaching the patient will be less. This is due to some loss of CPT on the walls of the syringes, needles and preparation vessels, which is prevalent with the Intralipid 20 suspension. When a carrier, such as cottonseed oil is used, this above-described loss is not so prevalent because CPT does not adhere as much to the surfaces of syringes, etc . . . For instance and preferable, it has been found that generally about 2.5 mg CPT/kg of body weight twice per week using cottonseed oil, administered by an intramuscular route, will deliver the same amount to the patient as 4.0 mg CPT/kg of body weight twice per week using Intralipid 20 as a carrier. Generally, about 1 mg to about 4 mg of CPT and/or derivatives thereof is added to about 0.1 ml to about 1 ml of carrier. Levels of both CPT and 9NO$_2$ were well tolerated by mice in the examples set forth below without weight loss or other signs of toxicity. These dosages have been administered for up to six months continuously without any ill effect.

Another important feature of the method provided by the present invention relates to the relatively low or no apparent overall toxicity of the camptothecin compounds administered in accordance herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. In one of the examples which follow, the overall toxicity of the camptothecin compounds of the present invention was evaluated. For example, CPT, when administered twice per week in amounts of 4 mg/kg in Intralipid 20 or 2.5 mg/kg in cottonseed oil, were found to be therapeutically effective (resulting in complete reduction of subcutaneous tumors) with no overall toxicity as described above. This was also the case when administering for more than 35 weeks the enormous total dose of 280 mg/kg.

Further, using 0.1 to 1.0 ml of cottonseed oil, in which CPT or derivatives were suspended, up to a quantity of 1 to 4 mg/kg were injected into the cavity of the stomach through a 27-gauge needle once a day for as long as desired (mice have tolerated more than 40 consecutive, daily injections) with no ill-effects.

The compounds of the present invention may be administered in combination with pharmaceutically acceptable carriers or diluents, such as Intralipid 10 or 20 or natural oils, or other suitable emulsifiers for lipophilic compounds.

The present invention will be further clarified by the following example, which is intended to be purely exemplary of the present invention.

EXAMPLE 1

Swiss nude mice of the NIH high fertility strain were bred and maintained pathogen-free in a laboratory. (Giovanella, B. C. and Stehlin, J. S. "Heterotransplantation of human malignant tumors in 'nude' thymusless mice. I. Breeding and maintenance of 'nude' mice." *J. Natl. Cancer Inst.* 51: 615–619; 1973.)

Human malignant carcinomas of the colon, breast, lung, ovary, stomach, pancreas, bladder, prostate, osteosarcoma and malignant melanomas were heterotransplanted directly from a patient into the nude mice and passaged serially. In particular, the tumors CLO, MUR, CAS, SW 48, SQU and BRO as described in Giovanella, B. C., Stehlin, J. S., Shepard, R. C. and Williams, L. J. "Correlation between response to chemotherapy of human tumors in patients and in nude mice." *Cancer* 52: 1146–1152; 1983), tumor SCH as described in Heim, S., Mandahl, N., Arheden, K., Giovanella, B. C., Yim, S. O., Stehlin, J. S., Jr. and Mitelman, F. "Multiple karyotypic abnormalities including structural rearrangements of 11P in cell lines from malignant melanomas." *Cancer Genet. Cytogent.* 35: 5–20; 1988, and Verschraegen, C., Giovanella, B. C., Mendoza, J. T., Kozielski, A. J. and Stehlin, J. S., Jr. "Specific organ metastases of human melanoma cells injected into the arterial circulation of nude mice." *Anticancer Res., In Press,* and tumor PC-3 as described in *Invest. Urol.* 17, 16–23, 1979, were used. Tumors DOY and HAR (undifferentiated non-oat cell carcinomas of the lung), DIL (a poorly differentiated squamous cell carcinoma of the lung), SPA (a moderately differentiated adenocarcinoma of the lung), LAN (an undifferentiated carcinoma of the ovary), and BRE (a moderately differentiated adenocarcinoma of the stomach) were heterotransplanted. For the experiments, the tumor tissue was finely minced in complete MEM medium and 0.5 ml of a 10% v/v suspension was inoculated subcutaneously on the upper back of groups of 10–30 mice. When the tumors became palpable and measurable in all the animals, they were divided into groups of 4–8 and treated with the desired dose of the drug in experiment or with the vehicle only for the controls.

9NO$_2$ (also referred to as 9NC) and 9AC were synthesized (Wani, M. C., Nicholas, A. W., Wall, M. E., "Plant Tumor Agents. 23. Synthesis and antileukemic Activity of Camptothecin analogues, *J. Med. Chem.,* 2358–2363, 1986) from CPT obtained from the Institute of Materia Medica, Academia Sinica, Shanghai, China. The derivatives were purified by chromatography and analyzed. A typical sample preparation for IM-injection or oral administration using Intralipid 20 or cottonseed oil for example includes the dispersion of the test compound by sonication (3 pulses for 30 seconds each) in Intralipid 20 or cottonseed oil at the standard concentration of 1 mg/ml using an Ultrasonic Processor, Model GE600 by Sonics and Materials, Inc., CT. Intramuscular injections were performed through a 27-gauge needle into the deep muscles of the posterior legs of the mice twice a week. The animals received up to 70 such injections consecutively without suffering ill effects except for some local fibrosis. Intravenous injections, using Intralipid 20 as the suspending agent, were performed through a 30-gauge needle in one of the tail veins. No pulmonary embolism was observed after over 200 injections.

Oral administration was achieved by mixing the required amounts of drugs in Intralipid 20 or cottonseed oil with a previously autoclaved dietary supplement composed of whole wheat bread saturated with whole milk. The supplement containing the drug was then thoroughly mixed to form a paste. Mice were fed 1 g of dietary supplement containing the required dose of the drugs once a day, and then 5 g of autoclaved mouse feed. (At this regime, the animals initially lose about 4 g out of 30 g of body weight, regain 2 g within a few days, and stabilize at this level). This regime can be carried on indefinitely. Actually, the mice fed in this manner (a slightly lower maximum caloric intake) were healthier and longer-lived than mice fed ad lib (Giovanella, B. C., Shepard, R. C., Stehlin, J. S., Venditti, J. M. and Abbott, B. J. Calorie restriction: Effect on growth of human tumors heterotransplanted in nude mice." *J. Natl. Cancer Inst.* 68: 249–257; 1982).

Figure 10:
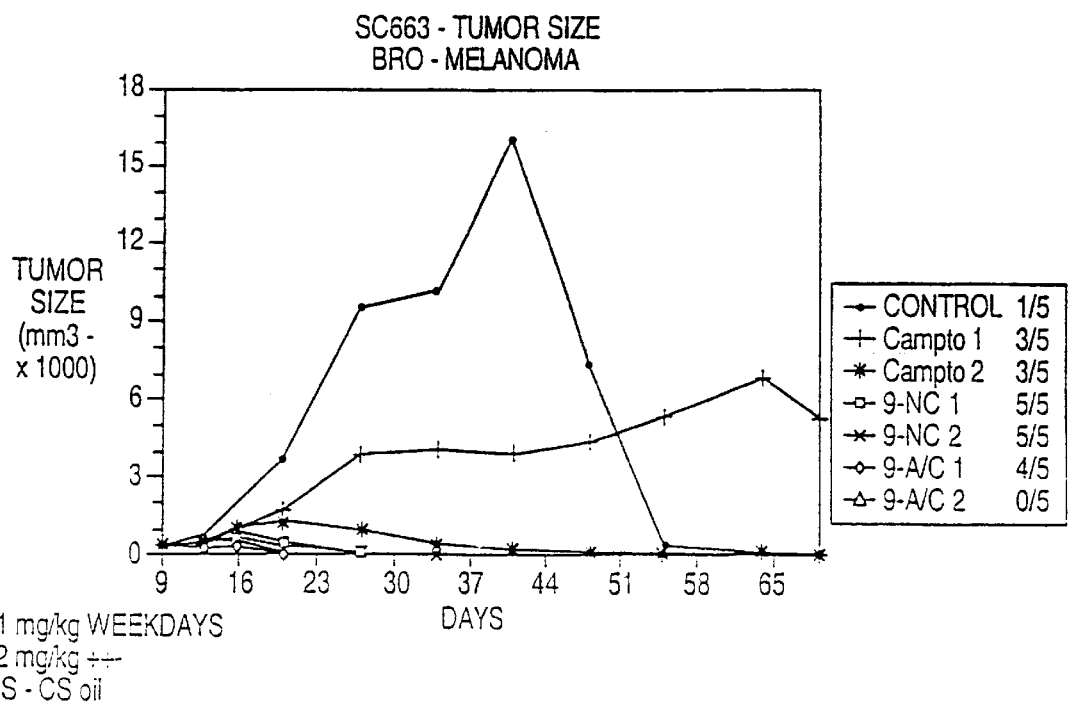
FIGS. 10 and 11 are graphs which show the results obtained for BRO melanoma in nude mice treated with 20(S)-CPT or CPT derivatives at various dosages by intrastomach means.
Figure 11:
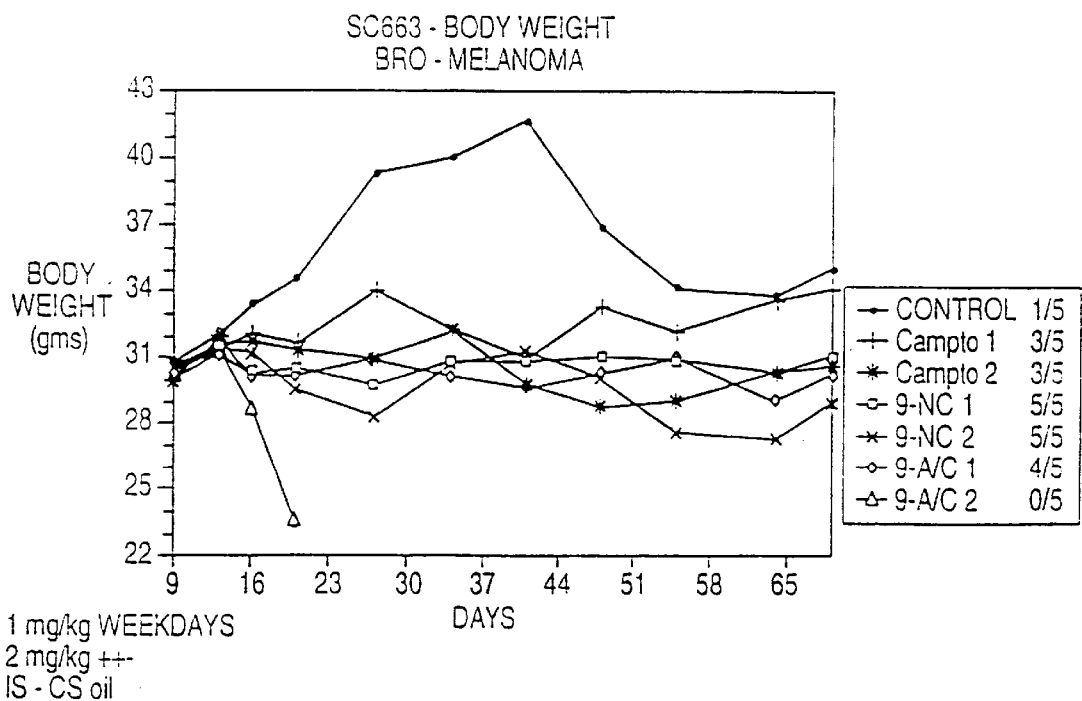
Figure 16:
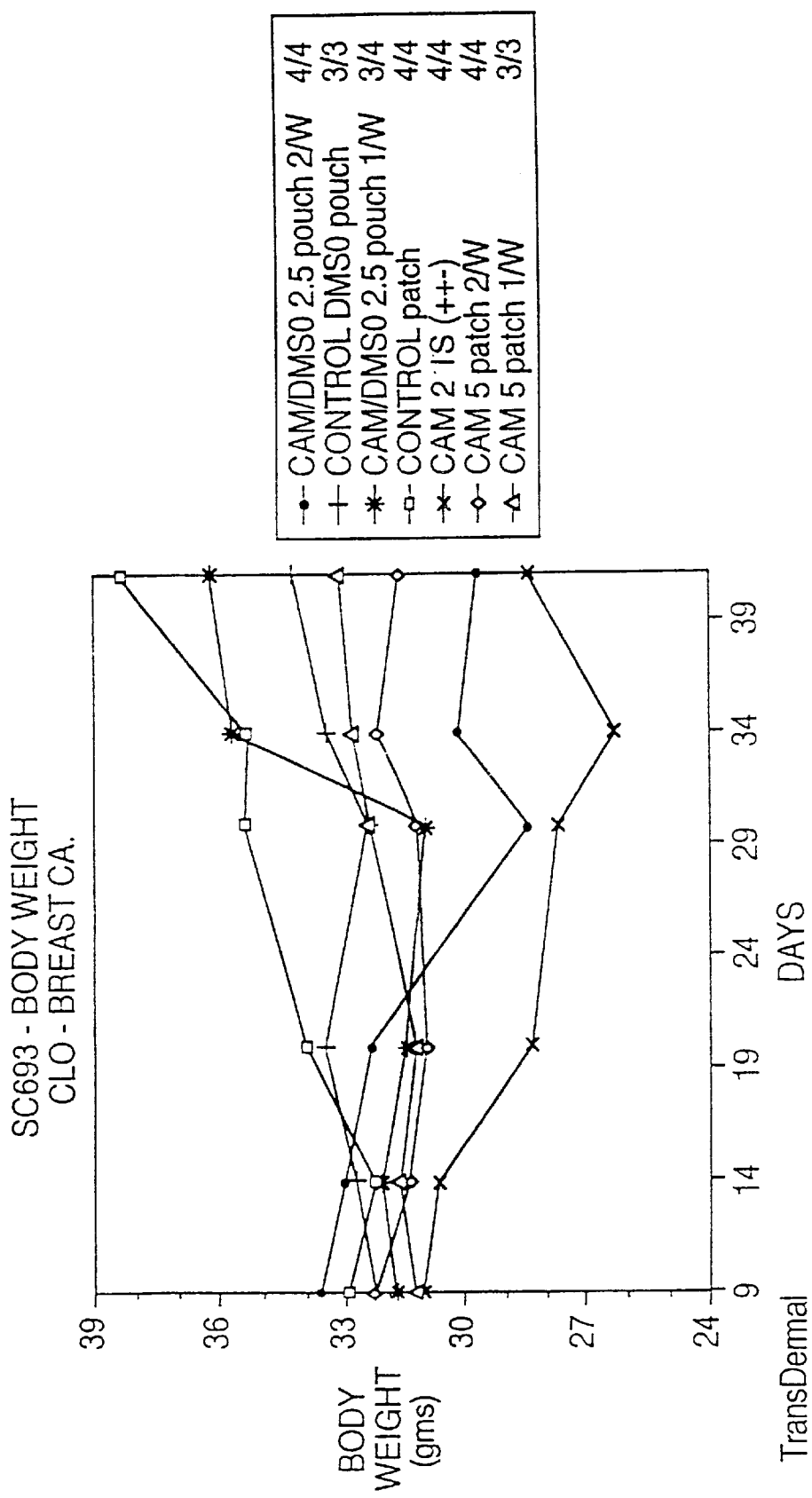

For the experiments and data reflected in FIGS. 10–11 and one experiment in FIGS. 16–17,oral administration was accomplished by injecting the mixture of CPT compound with cottonseed oil directly into the stomach (IS).

Table 1 summarizes some of the results obtained by this treatment with CPT and derivatives thereof.

TABLE 1

| TUMOR | TREATMENT | NO. ANIMALS | RESULTS | NO. TREATMENTS | OBSERVATIONS |
|---|---|---|---|---|---|
| BREAST Ca. | | | | | |
| CLO | IM CA 4 mg/kg | 12 | 10/12 CR | CR 58-29[1] | Alive day 170; Control 6/6 dead from day 120. |
| MUR | IM CA 4 mg/kg | 6 | 5/6 CR | 55 | 5/6 Alive day 180. Controls 1/6 alive. |
| | IM 9NO$_2$CA 4 mg/kg | 6 | 6/6 CR | 54 | 4/6 Alive day 180. Controls 1/6 alive. |
| COLON Ca. | | | | | |
| CAS | IM 9-AC 4 mg/kg | 6 | 5/6 CR | 20 | |
| | IV CA 4 mg/kg | 6 | 6/6 NR | 20 | |
| | IM CA (Na$^+$)4 mg/kg | 6 | 6/6 NR | 20 | |
| | IV Ca(Na$^+$) 4 mg/kg | 12 | 12/12 NR | 20 | |
| | IM 9-AC 4,8 mg/kg | 6 | 3/3 CR | 18 | |
| | IV 9-A/C 4 mg/kg | 3 | 3/3 CR | 18 | |
| | IM 9-NO$_2$CA 4 mg/kg | 6 | 2/3 CR | 23 | |
| | IM CA 4 mg/kg | 6 | 5/6 GI | 28 | Growth inhibited for 34 days. Controls all dead days 105. |
| | IM CA 4 mg/kg | 5 | 5/5 GI | 24 | Growth inhibited for 21 days. Controls 4/6 dead day 20. |
| | IV CA 4 mg/kg | 5 | 2/5 PR | 24 | |
| | IM CA 4,6 mg/kg | 10 | 9/10 CR | 9 | |
| | IV CA 4,6,8 mg/kg | 15 | NR | 9 | |
| SW 48 | IM CA 4 mg,kg | 14 | 14/14[2] GI | 1×/wk = 14T 2×/wk = 29T | Growth inhibited for 30 days. |
| SQU | IM CA 4 mg/kg | 7 | 7/7 GI | 21 | Growth inhibited for 73 days. All alive day 112. Controls 3/7 alive. |
| LUNG Ca. | | | | | |
| SPA | PO CA 4,6,8 mg/kg | 12 | 10/12 CR | 110 | |
| | IM CA 4 mg/kg | 6 | | 47 | Treated. All alive day 180. |
| | IM 9-NO$_2$CA 4 mg/kg | 6 | 9/12 CR | 47 | Treated. All alive day 180. Controls 6/6 dead day 153. |
| DOY | IM CA 4 mg/kg | 6 | 6/6 CR | 56 | All treated. Alive day 190. Controls 6/6 dead day 146. |
| HAR | IM CA 4 mg/kg | 5 | 4/5 CR | 41 | All treated. Alive day 167. |
| | IM 9-NO$_2$CA 4 mg/kg | 5 | 5/5 CR | 41 | All treated. Alive day 163. Controls 3/4 alive. |
| DIL | IM CA 4 mg/kg | 6 | 6/6 CR | 48 | All treated. |
| | IM 9-NO$_2$CA 4 mg/kg | 6 | 5/6 CR | 48 | Alive day 185. Controls 5/6 still alive. |
| OVARIAN Ca. | | | | | |
| LAN | IM CA 4 mg/kg | 8 | 8/8 CR | 27 | All treated. Alive day 83; |
| | IM 9-NO$_2$CA 4 mg/kg | 8 | 8/8 CR | 27 | controls 1/8 alive. |
| | IM 9-NO$_2$CA 4 mg/kg | 12 | 12/12 CR | 21 | Alive day 66. Controls 2/6 alive; all treated. |
| STOMACH Ca. | | | | | |
| BRE | IM CA 6 mg/kg | 5 | 5/5 CR | 36 | |
| | IV CA 6 mg/kg | 5 | 5/5 PR | 36 | |
| MAL. MELANOMA | | | | | |
| BRO | IM CA 4 mg/kg | 7 | 5/7 CR | 51 | All treated. Alive day |
| | IM 9-AC 4 mg/kg | 7 | 7/7 CR | 15 | 170. Controls 7/7 dead day 60. |
| | IM 9-NO$_2$CA 4 mg/kg | 14 | 14/14 CR | 21 | Alive day 60. Controls 2/7 alive. All treated. |
| SCH | IM CA 4 mg/kg | 8 | 8/8 GI[3] | 25 | Growth inhibited for 60 days. |
| | IM 9-NO$_2$CA 4 mg/kg | 8 | 8/8 GI | 25 | Growth inhibited for 30 days. |

[1]5 treated once a week
[2]7 treated once a week
[3]Tumor growth inhibited
CR - Complete remission defined as total disappearance of the initial tumor, maintained for at least 30 days at the making of this table
NR - No response
PR - Partial response
GI - Growth inhibited
CA - Camptothecin
9-AC - 9-Amino Camptothecin
9-NO$_2$CA - 9-Nitro Camptothecin
W - Week
D - Daily
Unless otherwise noted, all i.m. and i.v. doses are administered 2× week, all oral doses daily.

Figure 1B:
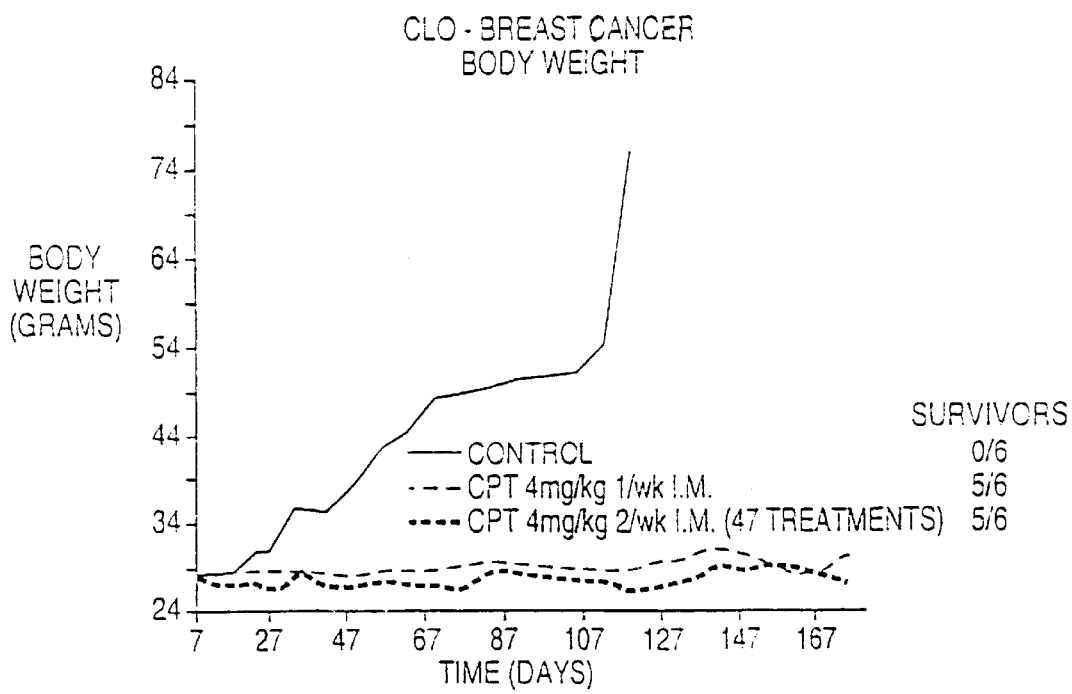
FIG. 1b depicts the results of the same experiment as FIG. 1a in body weight in grams of the nude mice carrying CLO breast carcinoma.

FIG. 1a shows the effectiveness of CPT against the human breast cancer when administered intramuscularly. FIG. 1b indicates that even prolonged intramuscular administration of the compound of the present application do not have any effect on the body weight of the mice at the dosage of 4 mg/kg using Intralipid 20 as the carrier. FIG. 2 shows the results obtained by treating a human lung cancer xenograft by oral administration of CPT. It is important to note that it is possible to administer CPT in Intralipid 20 without any toxicity at 8 mg/kg/day which is twice that of a 4 mg/kg/day dose which was already sufficient to totally suppress the tumor growth. FIG. 3 compares the effectiveness of the intramuscular versus the intravenous route of administration of CPT and the sodium salt derivative in side-by-side experiments. It can be seen that the sodium salt of CPT is completely ineffective regardless of its route of administration and regardless of the carrier used (Intralipid 20 or PBS). Furthermore, FIG. 3 leads to the conclusion that in comparing intramuscular administration with intravenous administration, the intramuscular route is the effective route. In other words, in viewing FIG. 3, the difference in anti-cancer activity of CPT can be appreciated when comparing intravenous administration versus intramuscular administration and the form of CPT used. In fact, using CPT Na+, the inventors were never able to eradicate human cancer xenografts, even when the most sensitive human tumors were used. Raising the dose of CPT Na+ brought on toxicity, causing first weight loss and then animal death without achieving total tumor regression. These findings were very similar to the unsuccessful clinical trials of the sixties and seventies discussed above.

Figure 4:
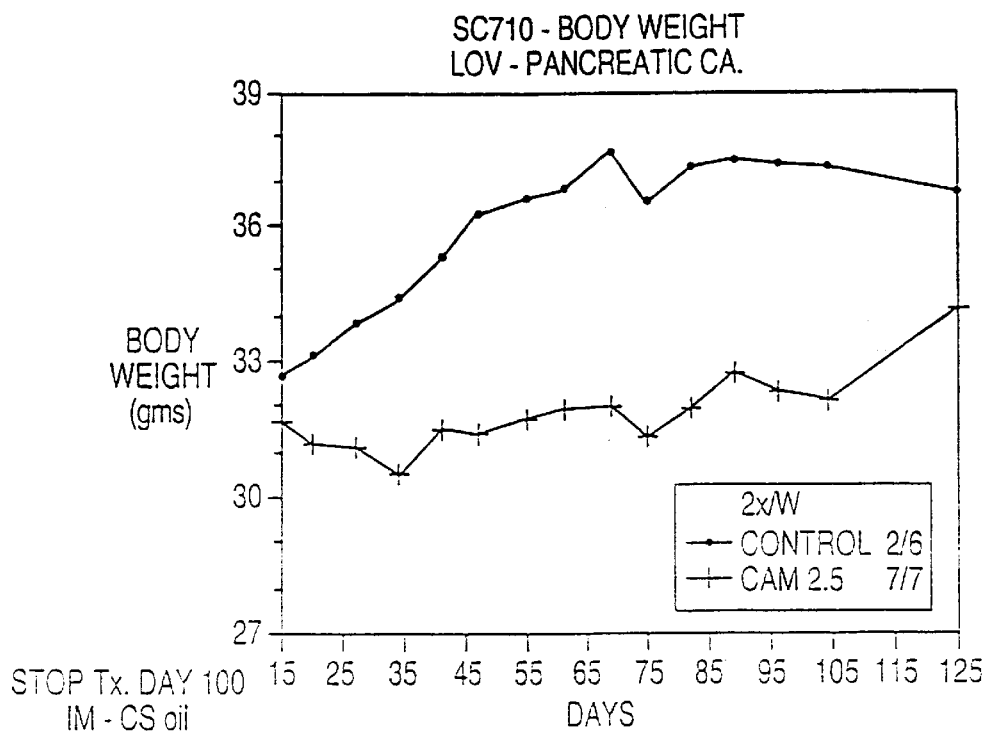
FIGS. 4 and 5 are graphs which show the results obtained for LOV pancreatic carcinoma in nude mice treated twice a week with 20(S)-CPT in cottonseed oil administered intramuscularly at the dose of 2.5 mg/Kg.
Figure 5:
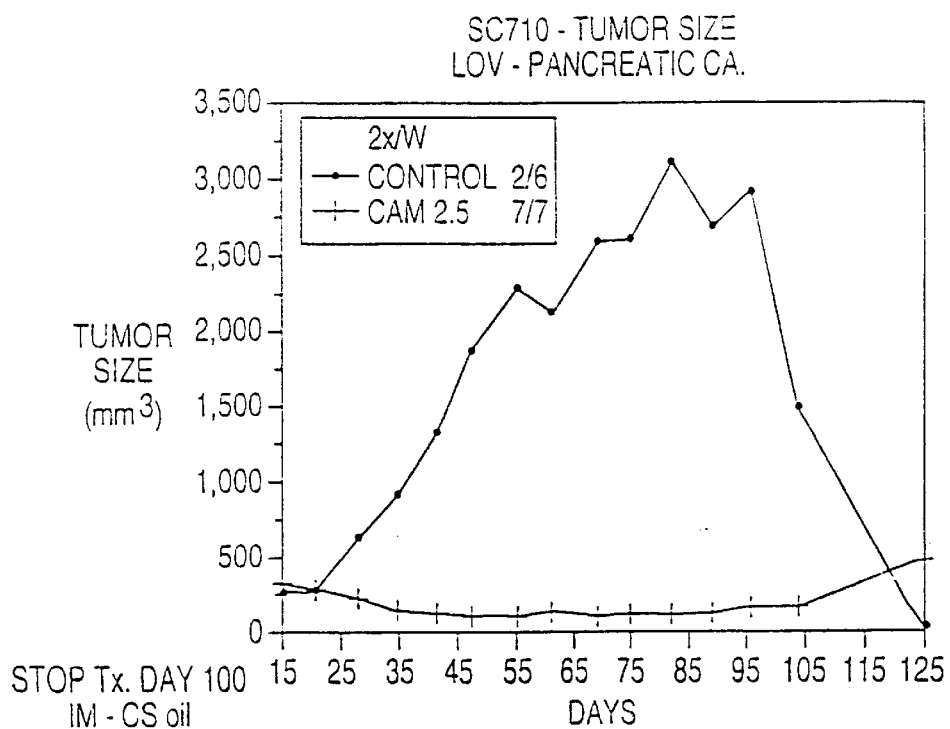

FIGS. 4 and 5 show the results obtained for LOV pancreatic cancer. Seven nude mice were treated intramuscularly with 2.5 mg/Kg body weight of 20(S)-CPT in cottonseed oil twice a week until day 100. Six additional nude mice were used as a control (cottonseed oil only). After 125 days, all mice receiving 20(S)-CPT survived as compared to only two of the six mice in the control group.

Figure 6:
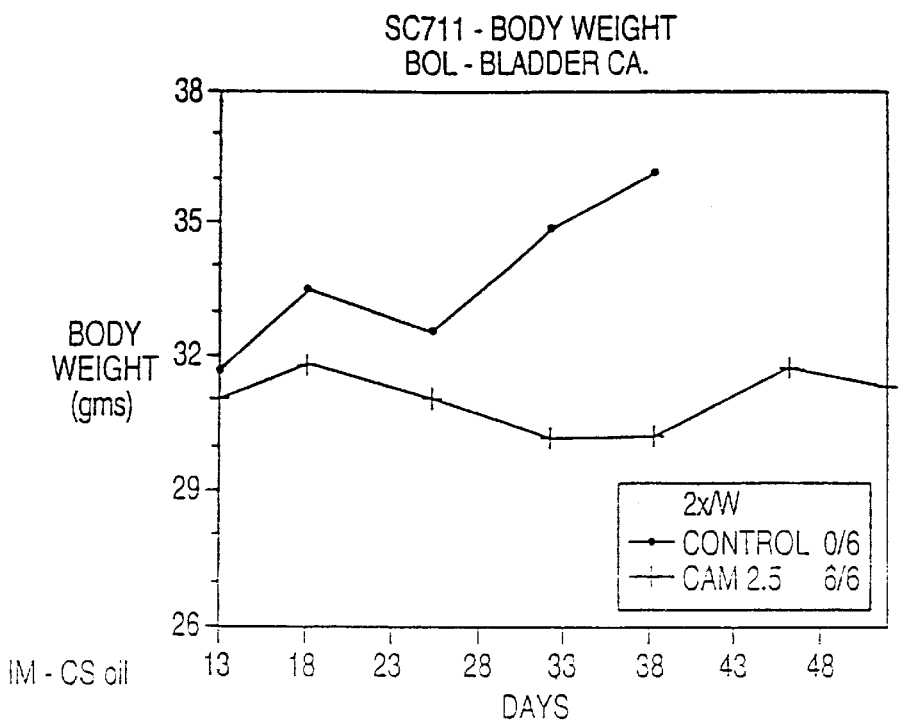
FIGS. 6 and 7 are graphs which show the results obtained for BOL bladder carcinoma in nude mice treated twice a week with 20(S)-CPT in cottonseed oil administered intramuscularly at the dose of 2.5 mg/Kg.
Figure 7:
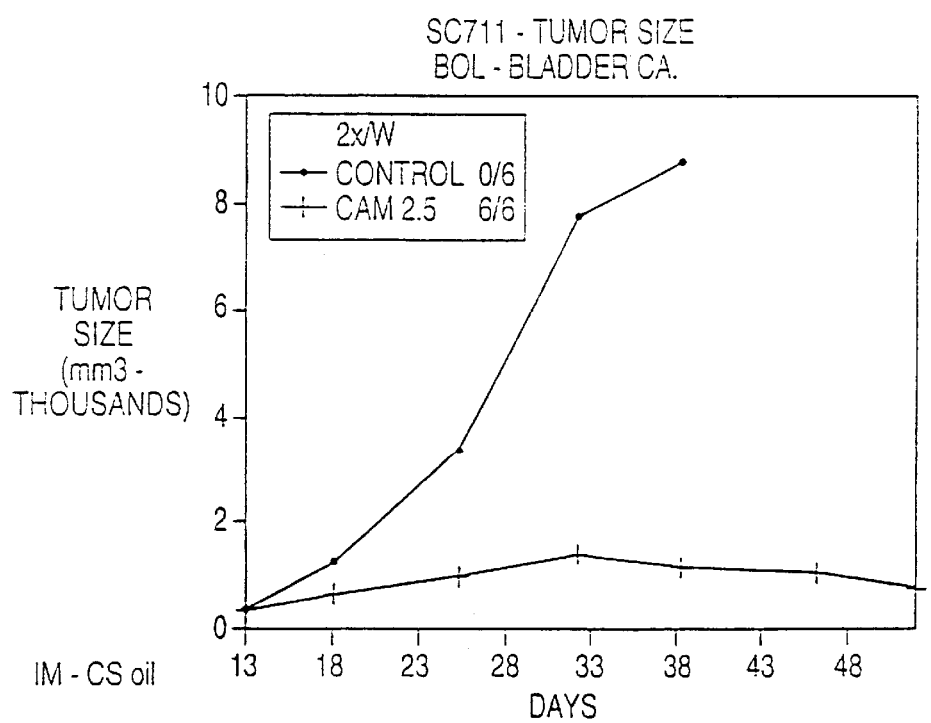

FIGS. 6 and 7 show the results obtained for BOL bladder cancer. Six nude mice were treated intramuscularly with 2.5 mg/Kg body weight 20(S)-CPT in cottonseed oil twice a week for 52 days. Six additional nude mice were used as a control (cottonseed oil only). All control mice were dead as of day 46, while all mice receiving 20(S)-CPT survived when the experiment was concluded (day 52).

Figure 8:
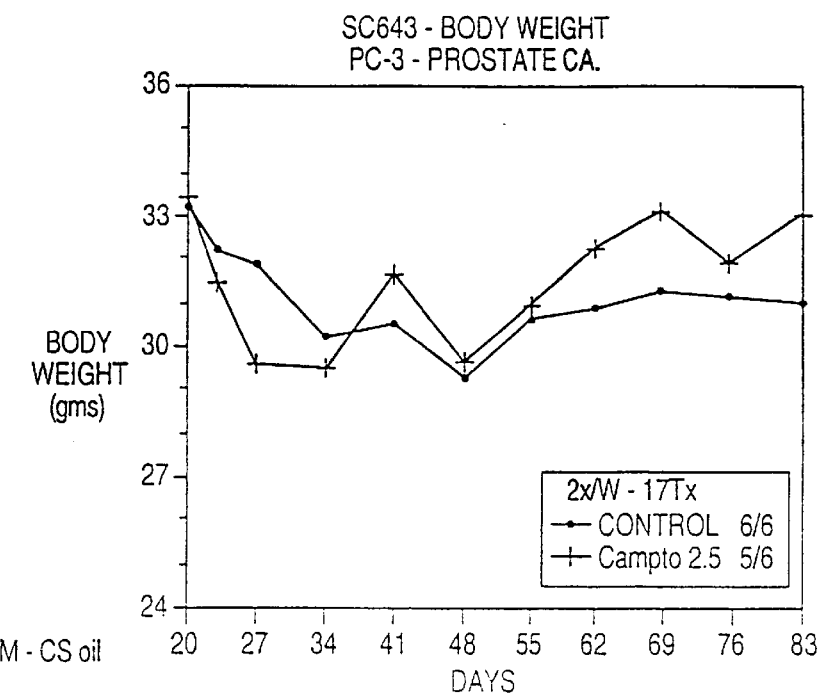
FIGS. 8 and 9 are graphs which show the results obtained for PC-3 prostate carcinoma in nude mice treated twice a week with 20(S)-CPT in cottonseed oil administered intramuscularly at the dose of 2.5 mg/Kg.
Figure 9:
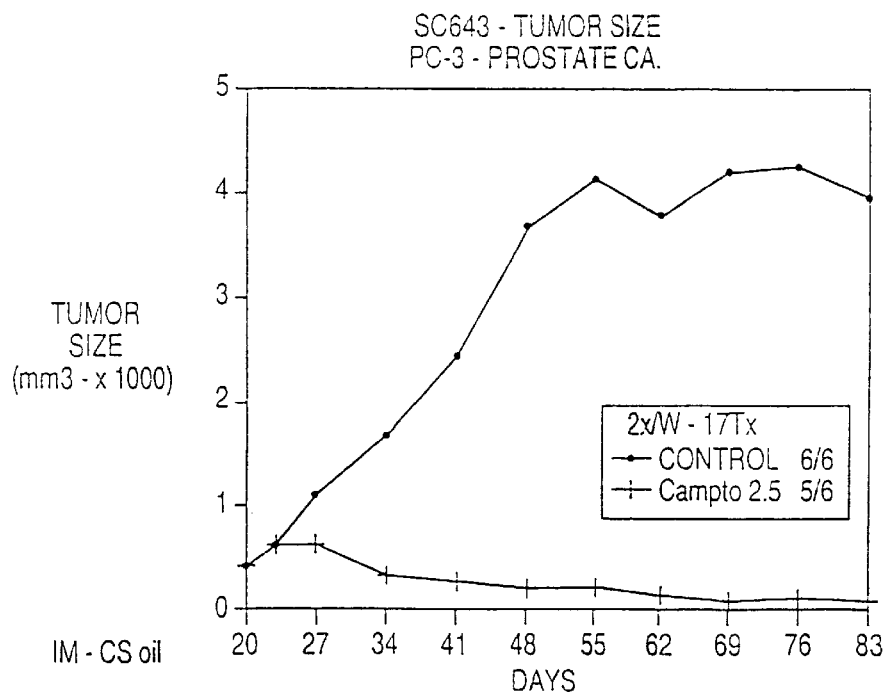

FIGS. 8 and 9 show the results obtained for PC-3 prostate cancer. Six nude mice were treated intramuscularly, with 2.5 mg/Kg body weight 20(S)-CPT in cottonseed oil twice a week for a total of 17 treatments. Six additional nude mice were used as a control (cottonseed oil only). After day 83, all mice survived except for one mouse receiving 20(S)-CPT.

FIGS. 10 and 11 show the results obtained for BRO-melanoma. Five nude mice were treated inter-stomach with 1 mg/Kg body weight 20(S)-CPT in cottonseed oil per day for 5 consecutive days with 2 day intervals of no treatment (i.e., 5 days of treatment then 2 days no treatment, and then 5 days treatment and so on). Five nude mice received 2 mg/Kg body weight 20(S)-CPT in cottonseed oil per day for two consecutive days with 1 day intervals of no treatment. Four additional groups of five mice each received in the exact same manner either 9-NC or 9-AC and one additional group was a control (cottonseed oil only) as reflected in FIGS. 10 and 11 and Table 2.

TABLE 2

|  | Control | 20(S)-CPT (1) | 20(S)-CPT (2) | 9NC (1) | 9NC (2) | 9AC (1) | 9AC (2) |
| --- | --- | --- | --- | --- | --- | --- | --- |
| # of mice used | 5 | 5 | 5 | 5 | 5 | 5 | 5 |
| amount received (mg/Kg) | — | 1 | 2 | 1 | 2 | 1 | 2 |
| timing of admin. | — | 5 days on 2 days off | 2 days on 1 day off | 5 days on 2 days off | 2 days on 1 day off | 5 days on 2 days off | 2 days on 1 day off |
| # of mice surviving after day 72 | 1 | 3 | 3 | 5 | 5 | 4 | 0 |

Figure 12:
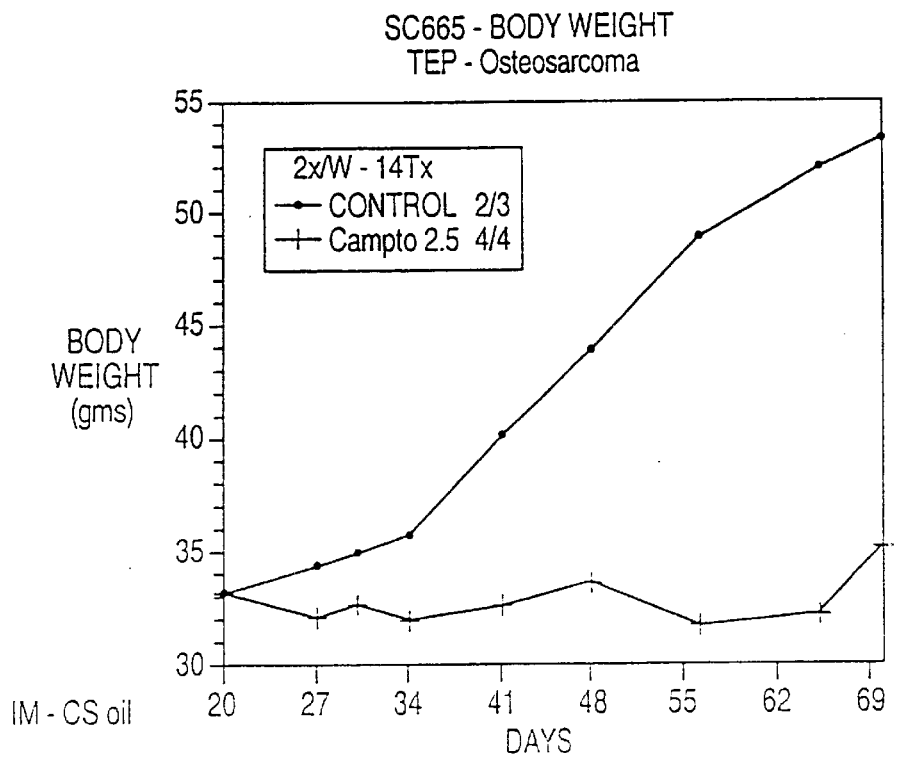
FIG. 12 and 13 are graphs which show the results obtained for TEP osteosarcoma in nude mice treated with 20(S)-CPT intramuscularly at the dose of 2.5 mg/Kg.
Figure 13:
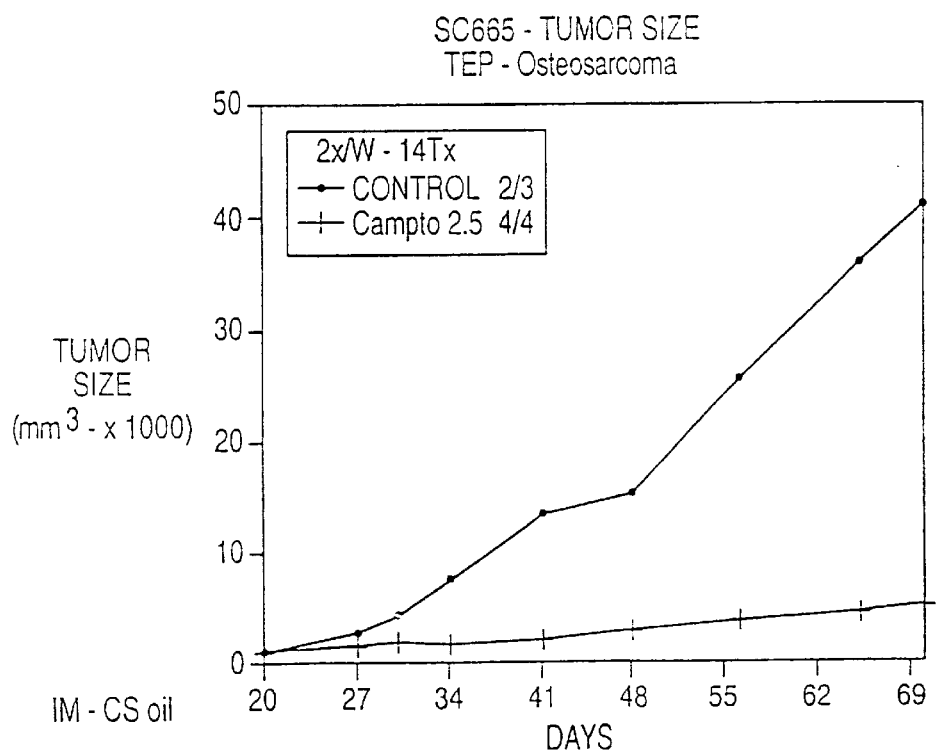

FIGS. 12 and 13 show the results obtained for TEP osteosarcoma. Four nude mice were treated intramuscularly with 2.5 mg/Kg body weight 20(S)-CPT in cottonseed oil twice a week for a total of 14 treatments. Three additional nude mice were used as a control (cottonseed oil only). After day 70, all mice survived except for one mouse in the control group.

Figure 14:
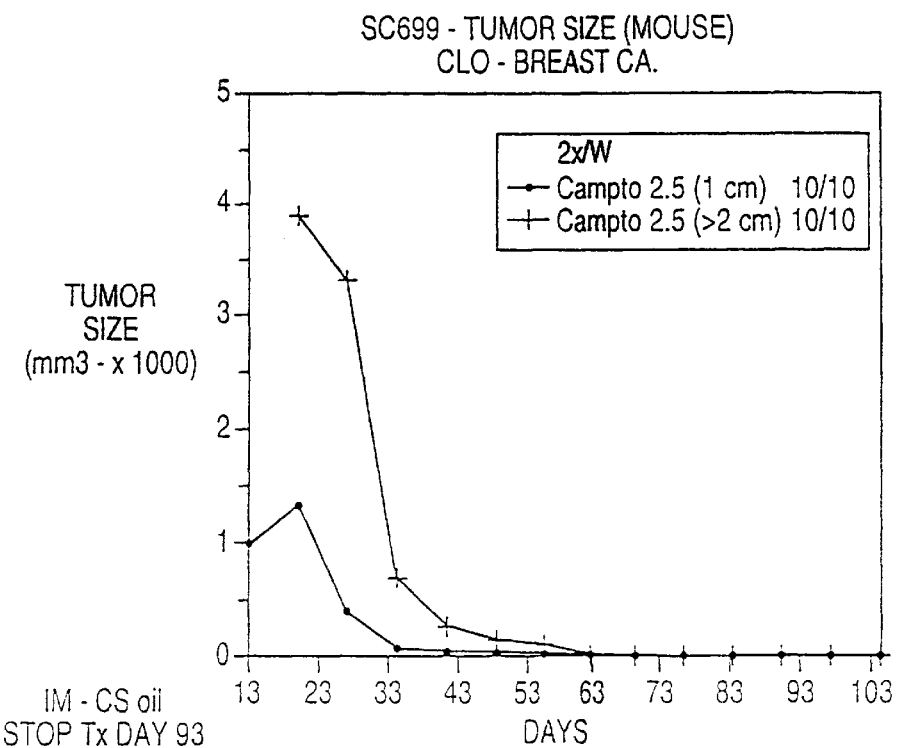
FIGS. 14 and 15 are graphs which show the effectiveness of 20(S)-CPT on different tumor sizes.
Figure 15:
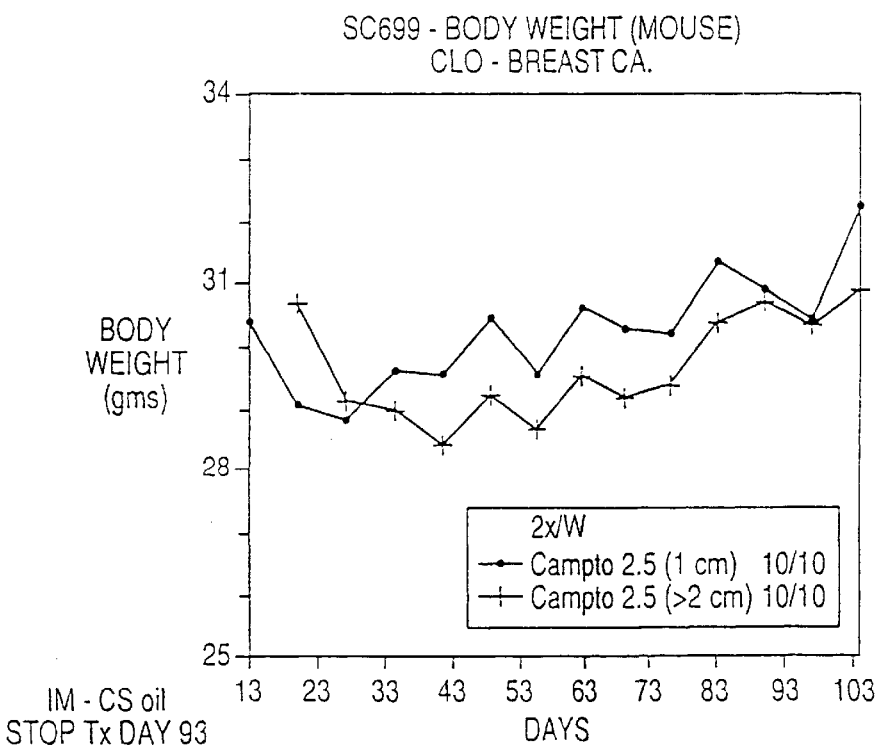

FIGS. 14 and 15 show the results of tumor response to 20(S)-CPT by treating two different sizes of CLO breast cancer tumors. In one group of 10 nude mice, tumor growth was allowed to get to one cm in size prior to treatment. In another group of ten nude mice, a tumor growth was allowed to get to 2+ cm in size prior to treatment. Each mouse in each group was then treated intramuscularly with 2.5 mg/Kg body weight 20(S)-CPT in cottonseed oil twice a week for 93 days. All mice survived when the experiment was ended on day 104. The experiment shows that tumor size effects the rapidity at which 20(S)-CPT regresses the tumor. In each group, 20(S)-CPT was not toxic to the mice and effectively regressed the tumor size.

It is clear from these studies, that CPT and its derivatives with the closed lactone ring have been demonstrated to possess an astonishing level of anticancer activity. This applies both to the spectrum of tumors covered and to the quality of the responses. The method of the present invention has been able to block growth completely and to totally regress human xenografts of carcinomas (lungs, breast, colon, stomach, pancreas, bladder, prostate, osteosarcoma and ovaries) and malignant melanomas. This has been accomplished without any observable toxicity. Many of the mammals which have been treated continuously for six months have shown no ill effects nor regrowth of the tumor they once carried.

EXAMPLE 2

Swiss nude mice of the NIH high fertility strain were bred and maintained pathogen-free in a laboratory. Human carcinoma of breast were heterotransplanted as described before in Example 1. For the experiment, CPT was purified to a purity of 99% as determined by HPLC. Two samples were prepared in the following manner:

1) 7.5 mg of CPT was mixed with 1 mL of dimethyl sulfoxide (DMSO) and after agitating for a minute, 4 mL of cottonseed oil was added and the mixture was transformed into a fine suspension by sonicating using an Ultrasonic Processor Model 2200 (Branson Ultrasonics Corp., Danbury CT 06810-1961) at 60° C. for one hour to yield a standard concentration of 2.5 mg/kg/0.05 mL.

2) 7.5 mg of CPT was dissolved in 5 mL DMSO with the help of sonication as described above for a final concentration of 2.5 mg/kg/0.05 mL. The two control mixtures were prepared by mixing cottonseed oil with DMSO in a ratio of 4:1, and the second control mixture consisting of DMSO alone.

The patches for the transdermal application consisted of sterile absorbent gauze from Johnson & Johnson (Skillman, N. J. 08558-9418) sheer bandages (¾ in. by 3 in.), which were pulled off from their adhesive backs and cut into thirds with the appropriate dimensions of 16 mm (±1 mm) by 8 mm (±1 mm). The appropriate amounts of suspended CPT were added. Tumor carrying mice were anesthestized with Avertin composed of a mother solution of 2.5 gm tribromoethanol and 50 mL tert. amyl alcohol, diluted with distilled water in a ratio of 1:30. After having mixed this solution, making sure that all had dissolved, the mixture was then filtered through a disposable sterile syringe filter (25 mm, 0.45 µm) by Corning Glass Works, Corning, N.Y. 14831. To induce sleep for the duration of the surgery (10 to 20 minutes) 0.8 mL/30 gm animal of this solution was injected via I.P. While asleep, the skin on the lower back of the animals was pulled together forming a pouch followed by stapling it almost completely shut, except for a small opening, through which the patch was inserted. The patch, which was inserted away from the tumor, was replaced twice a week using the same procedure above.

In further detail and as reflected in FIGS. 16 and 17, the following experiment was conducted.

(a) four nude mice each were treated with 2.5 mg/Kg body weight 20(S)-CPT in DMSO twice a week by means of the placement in the pouch without the use of a patch.

(b) Three nude mice each were treated with DMSO in a pouch as a control ("CONTROL DMSO pouch").

(c) Four nude mice each were treated with 2.5 mg/Kg body weight 20(S)-CPT in DMSO once a week by means of a pouch.

(d) Four nude mice each were treated with DMSO in cottonseed oil in a patch which was inserted in the pouch ("CONTROL PATCH").

(e) Four nude mice each were treated interstomach with 2.0 mg/Kg body weight 20(S)-CPT in a medium of DMSO/cottonseed oil for two day intervals with one day of no treatment in between (i.e., 2 days on then one day off and so on).

(f) Four nude mice each were treated with 5.0 mg/Kg body weight 20(S)-CPT in a medium of DMSO/cottonseed oil twice a week by means of a patch inserted into the pouch.

(g) Three nude mice each were treated with 5.0 mg/Kg body weight 20(S)-CPT in a medium of DMSO/cottonseed oil once a week by means of a patch inserted into the pouch.

The experiment was terminated at day 41. The survival rates were as follows:

(a) four survived
(b) three survived
(c) three out of four survived
(d) four survived
(e) four survived
(f) four survived
(g) three survived.

As can be seen from FIGS. 16 and 17, the body weight of the animals is more effected by the oral (I.S.) route than by the trans-cutaneous or transdermal route, although none of the animals in either group have shown any visual toxicity. Furthermore, when observing the tumor size, it may be pointed out that both the oral and the transdermal route of application showed good results in tumor regression.

The difference in applying CPT in a medium of DMSO versus DMSO/cottonseed oil shows that there is some dependence on the type of patch used in the experiments, and modifications in the application system may be made where the patch will show results superior to the oral route.

Other embodiments of the present invention will be apparent to those skilled in the art from consideration of the specification and practice of the present invention disclosed herein. It is intended that the specification and examples be considered as exemplary only, with a true scope and spirit of the invention being indicated by the following claims.

What is claimed is:

1. A method of treating a human lung cancer in a patient comprising administering intramuscularly or orally to said patient an effective amount of water-insoluble compound selected from the group consisting of 20(S)-camptothecin, 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, 11-hydroxy-20(S)-camptothecin, and mixtures thereof.

2. The method according to claim 1, wherein said compound is administered orally.

3. The method according to claim 1, wherein said compound is administered intramuscularly.

4. The method according to claim 1, wherein said compound is selected from the group consisting of 20(S)-camptothecin, 9-Nitro-20(S)-camptothecin and 9-Amino-20(S)-camptothecin.

5. The method according to claim 4, wherein said compound is administered orally.

6. The method according to claim 4, wherein said compound is administered intramuscularly.

7. The method according to claim 1, wherein said effective amount is from about 12.5 mg/m$^2$ of body surface per day to about 31.3 mg/m$^2$ of body surface per day in humans.

8. The method of claim 1 wherein said compound is 20(S)-camptothecin.

9. The method of claim 1 wherein said compound is 9-nitro-20(S)-camptothecin.

10. The method according to claim 9, wherein said compound is administered orally.

11. The method of claim 1 wherein said compound is 9-amino-20(S)-camptothecin.

12. The method according to claim 11, wherein said compound is administered orally.

13. A method of treating a human melanoma in a patient comprising administering intramuscularly, orally, or transdermally to said patient, an effective amount of a water-insoluble compound selected from the group consisting of 20(S)-camptothecin, 9-nitro-20(S)-camptothecin, 9-amino-20(S)-camptothecin, 7-ethyl-10-(4-(1-piperdino)-1-piperdino)-carbonyloxy-camptothecin, 7-ethyl-10-hydroxy-20(S)-camptothecin, 10,11-methylenedioxy-20(S)-camptothecin, 9-chloro-20(S)-camptothecin, 9-bromo-20(S)-camptothecin, 9-hydroxy-20(S)-camptothecin, 11-hydroxy-20(S)-camptothecin, and mixtures thereof.

14. The method according to claim 13, wherein said compound is administered transdermally.

15. The method according to claim 13, wherein said compound is 20(S)-camptothecin, 9-Nitro-20(S)-camptothecin, or 9-Amino-20(S)-camptothecin.

16. The method according to claim 15, wherein said compound is administered orally.

17. The method according to claim 15, wherein said compound is administered transdermally.

18. The method of claim 13, wherein said compound is 20(S)-camptothecin.

19. The method of claim 13, wherein said compound is 9-Nitro-20(S)-camptothecin.

20. The method according to claim 19, wherein said compound is administered intramuscularly.

21. The method according to claim 19, wherein said compound is administered transdermally.

22. The method of claim 13, wherein said compound is 9-Amino-20(S)-camptothecin.

23. The method according to claim 22, wherein said compound is administered orally.

24. The method according to claim 22, wherein said compound is administered intramuscularly.

25. The method according to claim 22, wherein said compound is administered transdermally.

26. The method of claim 13, wherein said compound is administered orally.

27. The method of claim 13, wherein said 9-Nitro-20(S)-camptothecin is administered orally.

* * * * *

UNITED STATES PATENT AND TRADEMARK OFFICE
CERTIFICATE OF CORRECTION

PATENT NO. : 5,889,017
DATED : March 30, 1999
INVENTOR(S) : Beppino C. GIOVANELLA, Hellmuth R. HINZ,
Anthony J. Kozielski, and John S. STEHLIN It is certified that error appears in the above-identified patent and that said Letters Patent is hereby corrected as shown below:

On the title page, item [75], add inventor --John S. Stehlin, Houston;--.

Signed and Sealed this

Fifteenth Day of February, 2000

Attest:

Q. TODD DICKINSON

*Attesting Officer*　　　*Commissioner of Patents and Trademarks*